US006838288B2

(12) United States Patent  
Beens

(10) Patent No.: US 6,838,288 B2  
(45) Date of Patent: Jan. 4, 2005

(54) MODULATOR FOR GAS CHROMATOGRAPHY

(75) Inventor: Jan Beens, TA Castricum (NL)

(73) Assignee: Thermo Electron S.p.A., Rodano (IT)

( * ) Notice: Subject to any disclaimer, the term of this patent is extended or adjusted under 35 U.S.C. 154(b) by 130 days.

(21) Appl. No.: 10/070,544

(22) PCT Filed: Nov. 28, 2001

(86) PCT No.: PCT/IB00/02253

§ 371 (c)(1),
(2), (4) Date: Apr. 16, 2002

(87) PCT Pub. No.: WO02/39106

PCT Pub. Date: May 16, 2002

(65) Prior Publication Data

US 2004/0185573 A2 Sep. 23, 2004

(30) Foreign Application Priority Data

Dec. 19, 2000 (IT) .................................. PCT/IT00/00532

(51) Int. Cl.[7] .............................................. G01N 30/30
(52) U.S. Cl. .......................... 436/161; 73/23.35; 95/86; 95/87; 96/102; 96/103; 96/104; 422/89
(58) Field of Search .......................... 422/89; 436/161; 73/23.35; 96/101, 102, 103, 104; 95/82, 86, 87

(56) References Cited

U.S. PATENT DOCUMENTS 5,032,151 A * 7/1991 Klein et al. .................... 95/17

FOREIGN PATENT DOCUMENTS

WO 98/21574 5/1998

OTHER PUBLICATIONS

CAPLUS Answer 2001:389513, Beens et al., J. Chrom., A (2001), 919(1), 127–132.*
E.B. Ledford Jr. et al; "Jet–Cooled Thermal Modulator FPR Comprehensive Multidimensioanl Gas Chromatography" Journal of High Resolution Chromatography; vol. 23, Apr. 13, 2000, pp. 202–204, XP000986878.
Marriott, Philip et al; "Cryogenic Solute Manipulation in Gas Chromatography–the Longitudinal Modulation Approach"; Trends in Analytical Chemistry, vol. 18, No. 2, 1999, pp. 114–125.

* cited by examiner

Primary Examiner—Jan M. Ludlow
(74) Attorney, Agent, or Firm—Nixon & Vanderhye PC

(57) ABSTRACT

This invention relates to a modulator for use in gas chromatographic analysis, adopted for alternatively trapping and releasing fractions of solutes in a length of a capillary column within a chromatographic oven, characterized in that it comprises at least one nozzle placed to spray at least one jet in at least one corresponding place along said capillary column length, said nozzle(s) being connected each to a source of liquid $CO_2$ via a related valve, and means for alternatively opening said valve(s) for a predetermined time, to cause a jet of liquid $CO_2$ to impinge for said predetermined time on said column place and to leave the oven atmosphere to heat said column place after said predetermined time. The modulator can be used in a conventional GC system or in a two dimensional GC system, for modulating the analytes fed to the second capillary column.

23 Claims, 7 Drawing Sheets

MODULATOR FOR GAS CHROMATOGRAPHY

This application is the U.S. national phase of international application PCT/IB01/02253 filed Nov. 28, 2001, which designated the U.S., which in turn claims priority from application PCT/IT00/00532 filed on Dec. 19, 2000.

FIELD OF THE INVENTION

This invention relates to a modulator for modulating sample fractions in a capillary column during a gas chromatographic analysis.

The modulator according to the present invention can be designed for a traditional gas chromatographic apparatus in order to enhance the sensitivity by narrowing the peaks when placed directly in front of the detector or to focus the injected analytes when placed directly after the injector. However, it con also specially designed for comprehensive two dimensional gas chromatography.

STATE OF THE ART

The comprehensive two dimensional gas chromatography, also called comprehensive 2D GC, or GCXGC, is a gas chromatographic technique in which the sample is first separated on a conventional normal-bore high-resolution capillary GC column in the programmed temperature mode. All of the effluent of this first column is then focused in a large number of extremely narrow (<100 ms) and adjacent fractions at regular, short intervals and subsequently injected onto a second capillary column, which is short and narrow to allow for very rapid separations. GCxGC can be interpreted as to exist of two GC systems coupled in series by means of a so-called modulation system (FIG. 1). The first GC is a conventional capillary GC system, including a conventional injector; the second is a fast GC, which is about 50 times faster than the first one. This is accomplished by using a short and narrow-bore column to provide very narrow peaks with peak widths at baseline of 100–200 ms. The modulation system provides the correspondingly narrow injection pulses in such a way that no sample is lost during the transfer between the chromatographic dimensions. In this way the comprehensive GCxGC technique permits to obtain a separation power considerably larger than that of conventional capillary gas chromatography, together with an improved sensitivity, a better peak identification and other advantageous features.

As previously said, in order to carry out said GCxGC it is necessary to operate a so-called modulation system between the first and second capillary column in order to retain and focus the narrow fractions of the effluent of said first column and inject the some at intervals onto said second column.

The most widely used modulators are of the thermal type, wherein a thermal action on a column length is used to trap and release the fractions to be injected in the second column.

The known heated modulators use an intermediate, thick film modulation capillary to trap (parts of) the eluting analytes from the first column by means of phase-ratio focusing. Heat is applied to thermally desorb the analytes from the thick film stationary phase in order to re-inject the narrow chemical pulses into the second column. FIG. 2 presents this phase-ratio focusing and thermally desorption process in four steps.

In the first paper describing the comprehensive GCxGC technique, by Liu and Phillips [Z. Y. Liu, J B. Phillips, *J. Chrom. Sci.*, 1991, 29,227–231] and in the Phillips patent [U.S. Pat. No. 5,196,039] a dual-stage metal-coated capillary with a thick film of stationary phase, connected with the outlet of the first column, but placed outside the oven, was employed as a modulation system. Sequentially the two parts of the metal coated capillary were resistively heated to desorb the analytes trapped due to the lower temperature of the modulation column and its thick stationary phase film. This system appeared not to be robust enough for long use and introduced limitations in the lower temperature of the oven housing of the two columns (as the minimum temperature of the oven should be in this case at least 100° C. higher than the temperature of the modulator which is kept close to the ambient one).

A more sophisticated heated desorption system was described and made commercially available by Ledford et al. [J. B. Phillips, R. B. Gaines, J. Blomberg, F. W. M. van der Wielen, J. M. Dimandja, V. Green, J. Granger, D. Patterson, L. Racovalis, H. J. De Geus, J. De Boer, P. Haglund, J. Lipsky, V. Sinha, E. B. Ledford, J. High Resolut. Chromatogr., 1999, 22, 3–10], and Phillips and Ledford patent [U.S. Pat. No. 6,007,602) mainly consisting of a slotted heater moving along the thick film capillary (sweeper) within the gas chromatographic oven.

However, this system too shows drawbacks, mainly due to the movement of the slotted heater in the close vicinity of the tiny capillary, which causes an easy breakage of the column and a limit of the oven maximum temperature.

In order to render more efficient the fraction trapping and eliminate the necessity of a special thick film capillary length, inserted between the first and second column as well as to remove the limitations related with the maximum oven temperature, so called cryogenic or cooled modulators were introduced.

These modulators, consisting of a cold trap moving sequentially forward and backwards along the inlet portion of the second capillary column (the cooling medium sweeps an upstream length of the second column), cryogenically trapping and focusing (parts of) the analytes as they elute from the first column on the first section of the second column itself [R. M. Kinghorn, P. J. Marriott, *J. High Resolut. Chromatogr.*, 1998, 21,620–622]. When the cryogenic system moves away from the zone in which the analytes were trapped, the surrounding GC-oven air quickly heats up the trapped analytes remobilising them for re-injection in the remaining part of the second column. This cryogenic trap, focus and re-injection process is schematically presented in FIG. 3.

The major drawback of this system is the very frequent breakage of the portion of the fused silica capillary column where the cold trap is moving due to ice formation between the cold trap and the column.

Apart from the mechanical differences between the heated and cooled modulators, there are also some differences in their applicability. In the heated modulators a difference in temperature of at least 100° C. is necessary between the oven and the sweeper, to remobilize the analytes from the thick film capillary that holds the retained fraction. The maximum temperature to which this capillary can be heated up, i.e. the maximum allowable temperature of its stationary phase, determines the maximum operation temperature of the sweeper.

The maximum temperature of the column oven will be therefore limited to 100 C. below the sweeper temperature and this introduces strong limitations in the application range covered by such systems. This limitation does not exist with the cooled moving modulator, the maximum operation temperature of the oven can be much higher as it is limited only by the maximum operating temperature of the two separation columns themselves.

The common characteristic of the thermal modulators as they have been described, however, is the fact that both techniques use a heating/cooling device that moves across a close distance around a fragile fused silica capillary column. Even very accurate (and rather tedious) tuning of these moving devices and their short distance to the capillaries, frequently leads to breakage of the tiny, and fragile capillaries.

Ledford [E. B. Ledford, C. Billesbach, *J. High Resol. Chromatogr.*, 2000, 23, 202–204] introduced a modification of its heating sweeper, by applying a cooling jet of $CO_2$ on the heating arm. However, this system and the cryogenic system as previously illustrated show all drawbacks of the modulators having movable parts within the oven and moreover the continuous jet of $CO_2$ tends to create ice formations on the column which involves, breaking possibilities and hindering of fraction release.

Ledford (E. B. Ledford, presented on the 23$^{rd}$ *Symposium on Capillary Gas Chromatography*, Riva del Garda, Italy, June 2000) recently proposed a two-stage liquid nitrogen/heated air let modulator with no moving parts. Two cooling and two heating jets spot-cool and heat a very short section of the second column to trap/focus and re-inject the modulated fractions. The two cooling jets of the two-stage jet modulator alternately spray liquid nitrogen directly onto the inlet part of the second column for trapping/focusing. Two jets with heated gas alternately heat up these spots to remobilize the analytes for re-injection as very narrow pulses.

The heating jets were necessary, since the temperature of the cooled sections of the second column could reach temperatures as low as 190° C.

Liquid nitrogen is not easily available at every laboratory and needs bulky insulation when transported through tubes. Moreover, the use of liquid nitrogen may create problems due to ice formation within the oven and in particular on the jet nozzles which may such hinder or even stop the release of liquid nitrogen. Moreover, since the hot air jet must have a temperature at least 100° C. above the oven temperature and very high air jet temperature cannot be reached for reasons of column integrity (maximum temperature of fused silica columns is 350° C.), this limits the maximum temperature of the oven and the range of applications covered by such systems.

OBJECTS OF THE INVENTION

The object of the present invention is now to provide a modulator for GC or GCxGC which optimises the analytes treatment in a conventional GC system and overcomes the drawbacks of the presently known modulators for GCxGC, in particular with reference to those connected with the mobile modulators (sweepers) and with the use of liquid nitrogen and hot air jets in the Ledford modulator with no moving parts.

DESCRIPTION OF THE INVENTION

The main feature and further features of the modulator according to this invention are reported in claim 1 and respectively in the dependent claims.

BRIEF DESCRIPTION OF THE DRAWINGS

The invention will be more deeply described with reference to the accompanying drawings, wherein.

DESCRIPTION OF THE PREFERRED EMBODIMENTS

Figure 1:
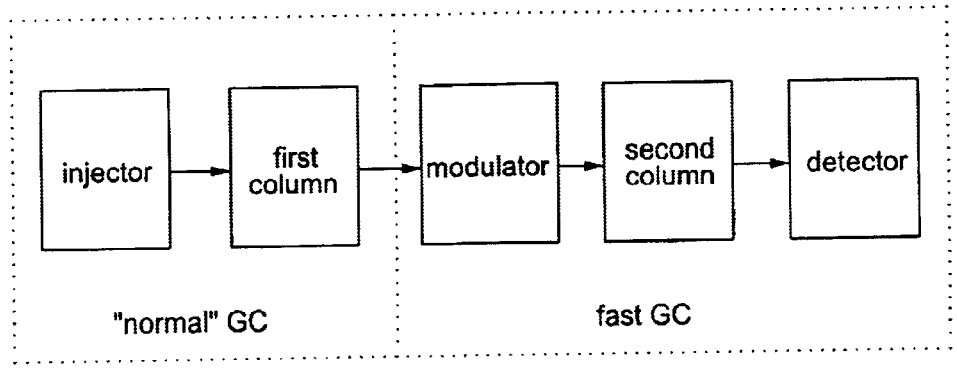
FIG. 1 is a scheme of the GCxGC system.
Figure 2:
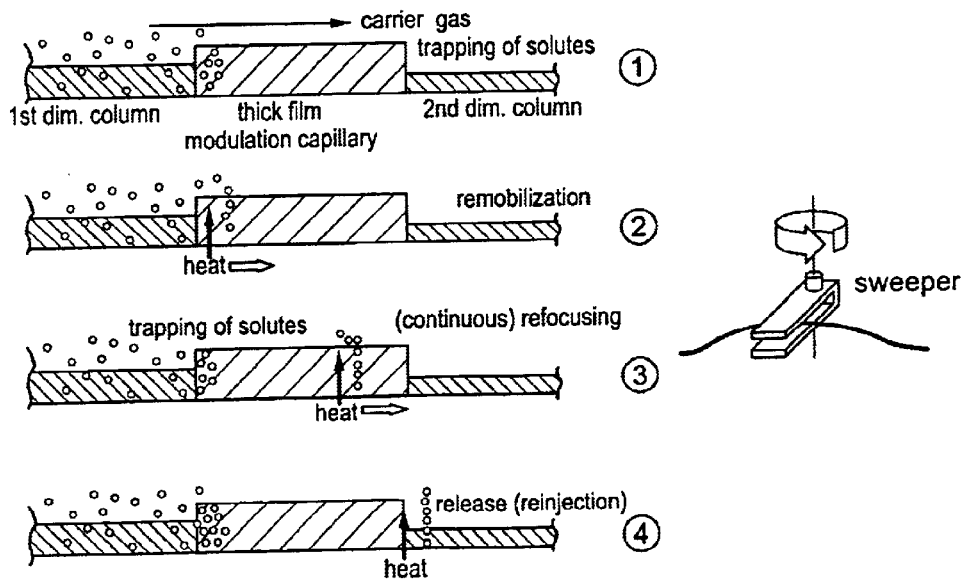
FIG. 2 is a scheme of the known heating modulation system (sweeper).

Referring to the drawings, FIG. 1 diagrammatically shows the components of a known GCxGC system, preferably housed in a single oven. FIG. 2 shows a scheme of the heating modulation process, in which the fraction eluting from the first column is trapped at the upstream end of the thick film of the modulation capillary (phase trapping) (step 1); when the heating sweeper comes in correspondence of this capillary upstream end, the heat effect releases the fraction (step 2) and transports the same along the thick film capillary, while a further fraction is trapped at the capillary upstream end (step 3).

When the sweeper reaches the second column, the first fraction is released on the same, while the further fraction is still trapped at the modulation capillary upstream end (step 4).

Figure 3:
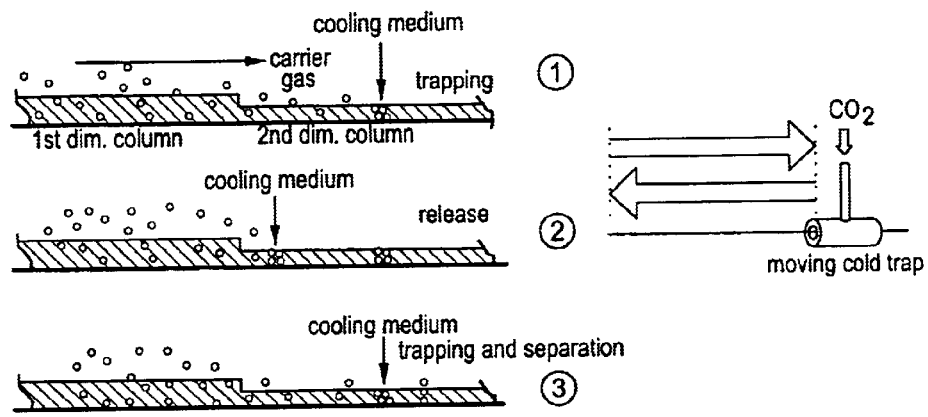
FIG. 3 is a scheme of the known cryogenic modulation system.

FIG. 3 schematically shows the cryogenic modulation process, wherein a cooling medium cools an upstream length of the second column. In correspondence of the cooling medium the fraction is trapped by thermal action and then released when the cooling medium is removed.

Figure 4:
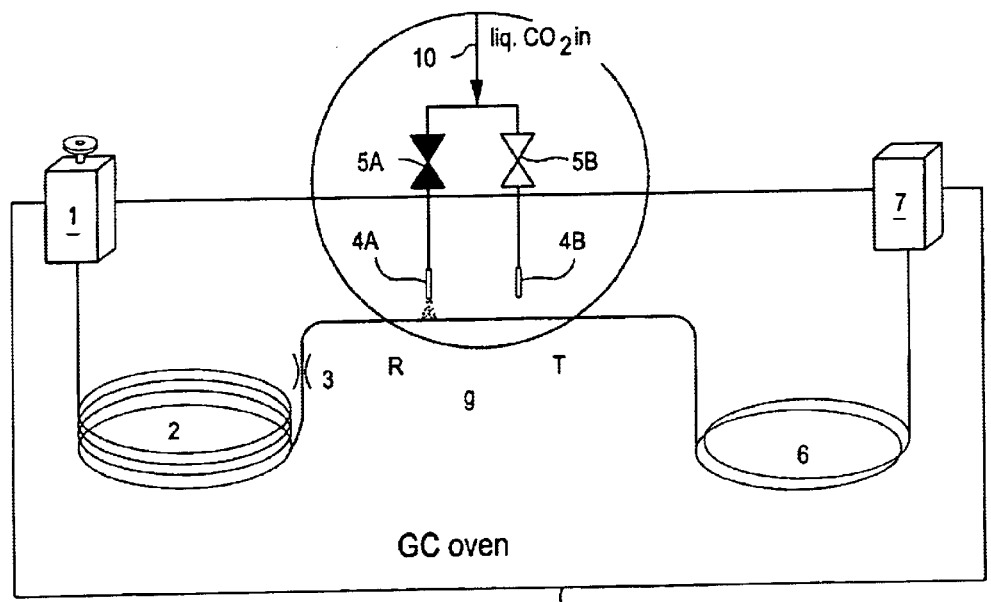
FIG. 4 is a scheme of a modulator according to the present invention.

FIG. 4 is a scheme of a GCxGC system with a modulator according to this invention. The system comprises, in a GC oven 8, an injector 1, a first column 2 and a second column 6 which are connected at 3 according to a well known technique. The second column 6 ends in a detector 7.

On an upstream length 9 of the second column 6 two jets 4A and 4B operate alternatively and at a suitable frequence, which are fed, through corresponding valves 5A and 5B, by a source of liquid $CO_2$ 10 so that two parts of the capillary length 9 are directly cooled alternating in order to trap and focus the fraction, whereafter they are remobilized by the heat of the surrounding oven air. The opening time of each valve is preferably the same for all valves and half the cycle time, while the opening and closure of the valves are carried out in sequence to cover a cycle time in the order of 0.1 to 30 seconds. It is to be noted that the opening time of said valves could also be different and that this opening time may vary from about 0.1 to about 30 seconds.

Figure 5:
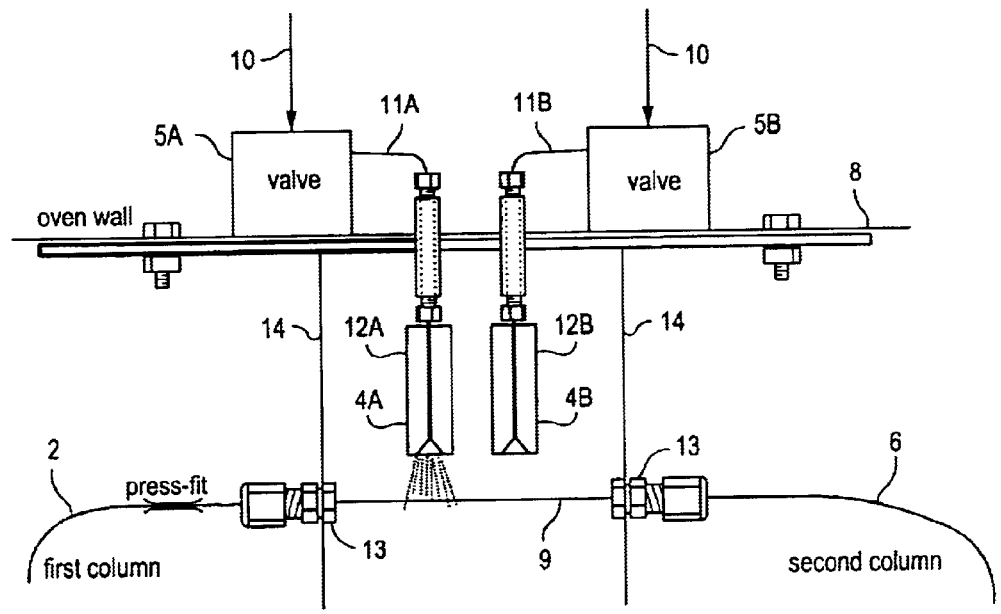
FIG. 5 is a detail of the jet configuration of the modulator of FIG. 5.

The $CO_2$ jets in FIG. 5 consist of two electrical-driven two-way valves 5A, 5B that open and close the liquid-$CO_2$ line alternating through two pieces of 40 mm long, 0.8 mm ID capillaries 11A/11B, coupled to the nozzles (12A, 12B), 50 mm long 0.5 mm ID capillaries. In order to force as much $CO_2$ from the outlet of the jets to touch the column, the outlets have been modified to form a slit, 0.04 mm wide and 3 mm long, in parallel above the capillary. To prevent ice formation onto the outside of the jets at oven temperatures below about 100° C., they have been inserted in a 12 mm diameter brass socket to increase the heat capacity.

Figures 10A, 10B:
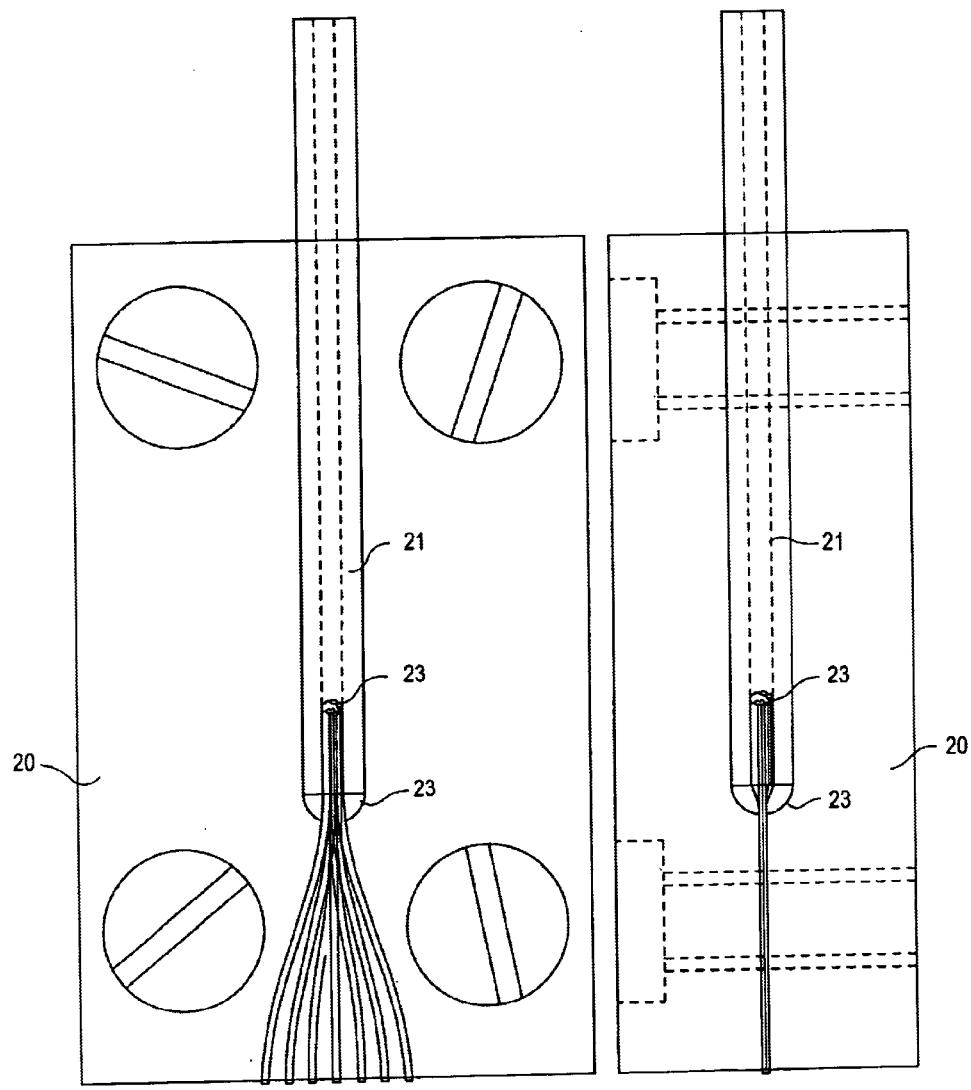
FIGS. 10*a* and 10*b* are diagrammatic representations of an alternative embodiment of the jet configuration, respectively in front view and side view.
Figure 11:
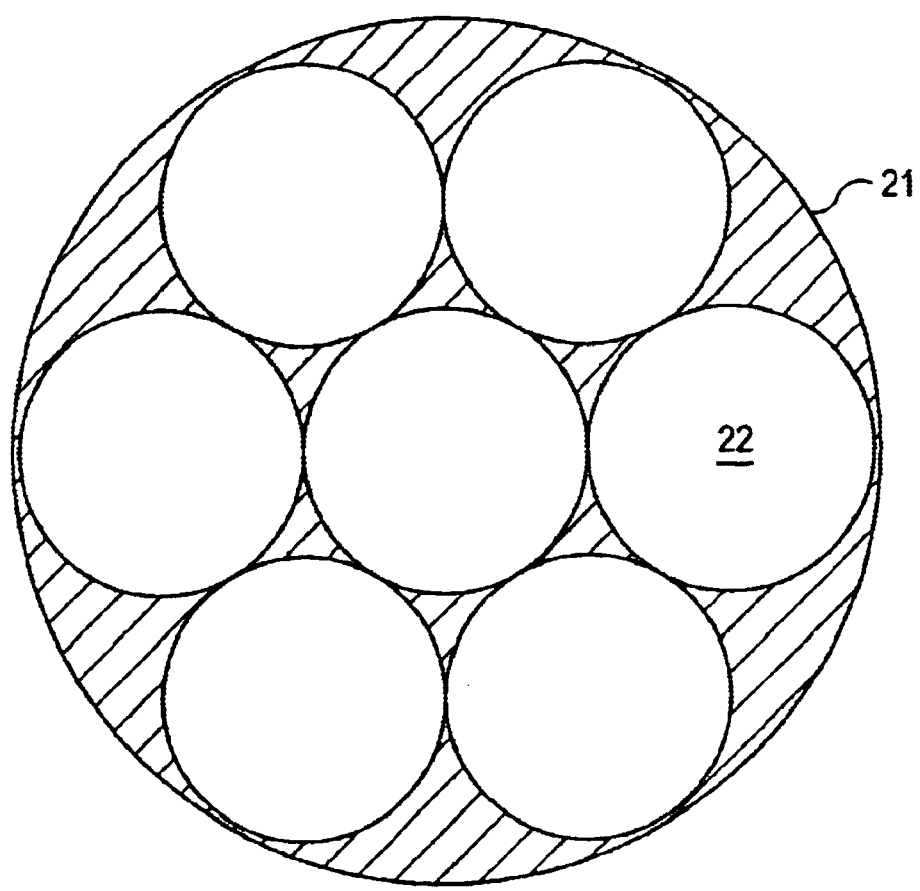
FIG. 11 is a diagrammatic end view of another alternative embodiment of the jet configuration.

An alternative embodiment of the jet configuration is shown in FIGS. 10a, 10b and 11, wherein, instead of the slit, the outlet is constructed by inserting a series of seven capillaries in a row between the same brass half blocks. More detailedly, as shown in FIGS. 10a and 10b, each brass block 20 houses a stainless steel capillary 21, for instance having 1/16" OD and 0.7 mm ID, said capillary 21 being connected through a related valve 15, to the $CO_2$ source 10. Within the end of capillary 21 are inserted for instance seven capillaries 22 placed according to what is shown in FIG. 11 and fixed preferably by a ceramic glue or soldering 23, which is able to withstand temperatures of up to 400° C. In the shown example the capillaries have the following dimensions: length 35 mm, OD 0.23 mm, ID 0.11 mm and their free portions are aligned so to run in parallel with the secondary GC column 9 so that an optimum heat exchange is enabled by generating a "curtain" of expanding $CO_2$.

The axes of the outlet openings of the capillaries 22 are placed 0.4 mm apart, so that the total length of the nozzle again is 3 mm. Of course, the above stated number and dimensions of capillaries can be changed at will.

The above stated construction allows to decrease the consumption of $CO_2$ and optimize the effectiveness of the throttling process at the nozzle outlet of the cryogenic jets.

As the liquid $CO_2$ expands at the outlet of the nozzles, the throttling process cools the departing gas through the Joule-Thompson effect. Since this gas is sprayed directly onto the second column length 9 at the prevailing flow, the column quickly cools down to about 100° C. below the oven temperature. Closing the valve will immediately stop the cooling process and the surrounding air from the stirred oven will heat up the short cooled section of capillary (about 10 mm) momentarily to oven temperature. The time required to heat the capillary column from cryogenic to oven temperature is only 13 ms for a normal 100 $\mu$m column (15 $\mu$m polyimide and 80 $\mu$m fused silica walls).

The length 9 of the second column in which the modulation takes place, is stretched and secured between two Valco unions 13 mounted on a bracket 14. The stretching is necessary in order to avoid vibration of the column caused by the rather intense flow of cold $CO_2$ that is sprayed onto the column. The unions are mounted onto two bonds of 1 mm thick, resilient steel in order to compensate for the difference in thermal expansion of the steel bracket and the fused silica column.

A simple timing device that generates the 24 DC voltages for valve switching controls the modulation process. Modulation times shorter than 0.3 seconds can be established.

In order to test the performance of the modulator according to the invention, a gas chromatograph was used with a split/splitless injector and a Flame Ionisation Detector capable to produce a digital signal sampled at 200 Hz rate. The first dimension column 30 m×0.32 mm ID was coated with methylsilicon polymer, 0.25 microns film thickness. It was coupled through a press-fit connector to the second is column 1.5 m×0.10 mm ID, which was coated, with 0.1 $\mu$m BPX50 (SGE International, Ringwood, Australia). The flow was set to 1.0 mL/min through a column head pressure of 170 kPa helium. The columns were temperature programmed from 50° C., 4 min isothermal, 2° C./min to 300° C.

Figure 6:
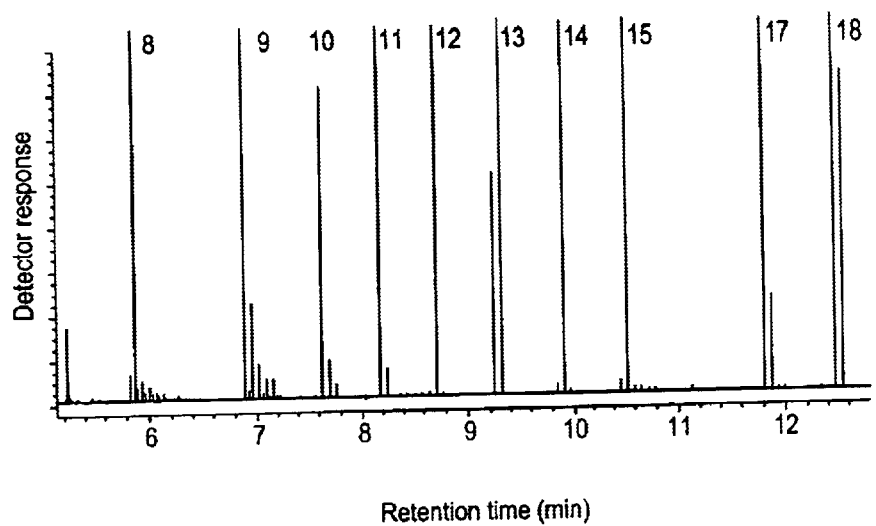
FIG. 6 is a chromatogram obtained by means of a GCxGC separation of $C_8$ through $C_{18}$ with a modulator according to the present invention.
Figure 7:
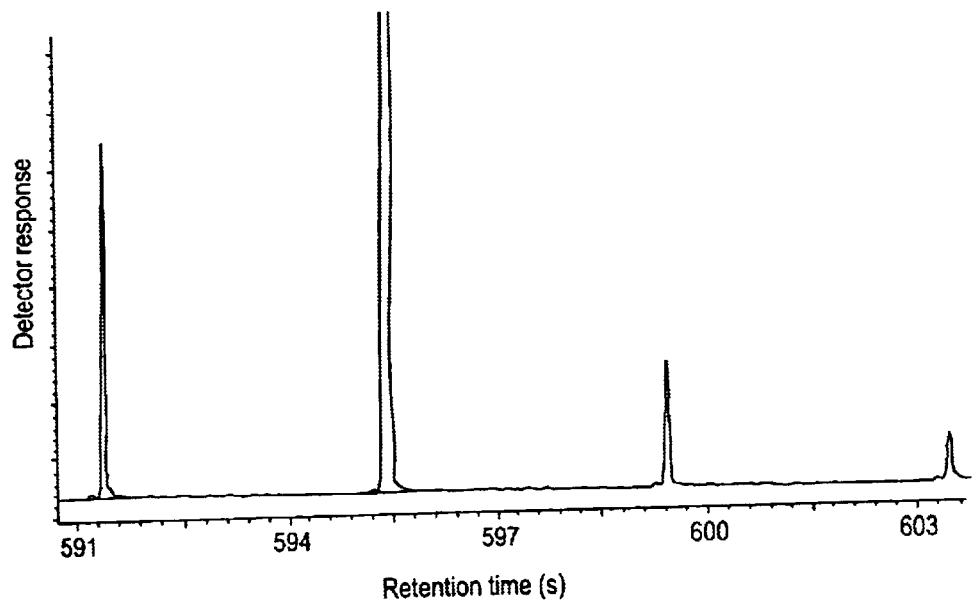
FIG. 7 is a chromatogram obtained by means of a GCxGC separation with a modulator according to the invention and showing the shape of the modulated n-$C_{14}$ peaks.

The main functions of the modulator are twofold: focusing small fractions from the effluents of the first column into narrow pulses and re-injection of these pulses into the remaining part of the second column. To judge the performance of the modulator, it is sufficient to measure or calculate the bandwidth of the injected pulses. To judge the performance of the dual jet modulator, a series of n-alkanes ($C_8$ through $C_{18}$, see FIG. 6) was separated. From calculations of the peaks modulated from n-C14 (see FIG. 7), the peak widths are $\sigma$=30 ms, which is better than second dimension peaks previously reported in the literature for known modulation systems (sweeper and cryomodulators). The injection bandwidth appeared to be $\sigma$<10 ms, which is also better than the injection bandwidths of the known sweeper and cryo modulators.

According to what stated above, the jet modulator of this invention is very simple in construction and easy to install and maintain. Its control is performed by simply switching one, two or more valves, so that no movable part are foreseen within the oven, thus preventing any column breakage due to movement of the previously known movable modulators.

Moreover, it has been ascertained that the ability of the modulator according to the invention to focus the trapped first dimension fractions into narrow pulses is superior to that of the modulators known, tested and described in the prior art.

Figure 8:
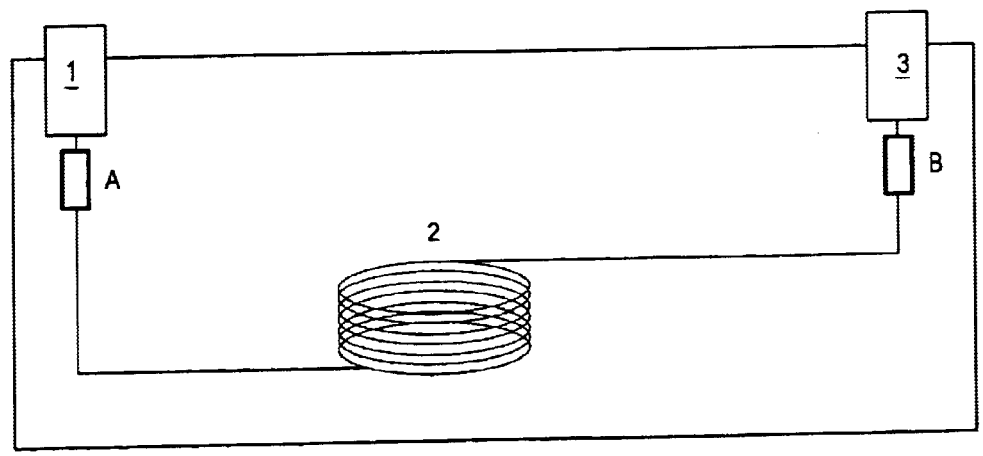
FIG. 8 is a scheme of a modulator according to the present invention when applied to a conventional GC system.

It is to be finally noted that the present modulator, when designed with one liquid $CO_2$ jet only, can act as an injection focusing device and/or as a peck narrowing and then a detector sensitivity enhancing device in a conventional one-dimensional GC system. This configuration is depicted in FIG. 8, where a capillary column 2 is conventionally housed in an oven and connected with an injector 2 and a detector 3. A jet of liquid $CO_2$ issued by a source outside the oven and controlled by a valve, placed outside the oven, con be foreseen to impinge on a column portion respectively directly after the injector (position A) and/or immediately before the injector (position B).

When in position A, the $CO_2$ jet allows to focus the injected analytes, while when in position B the jet enhances the sensitivity of the detector by narrowing the peaks.

Figure 9:
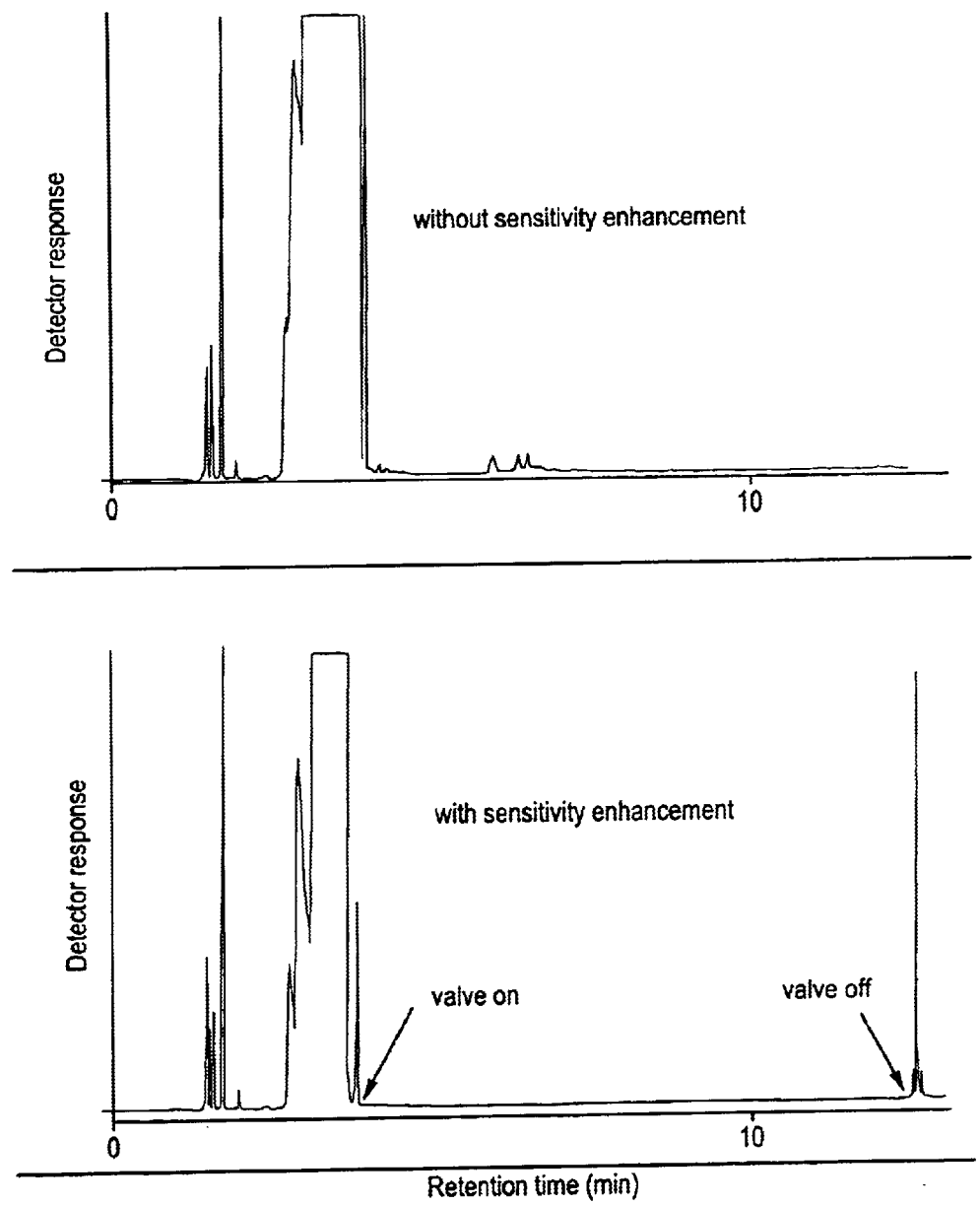
FIG. 9 represents two chromatograms showing the effect of peak sensitivity enhancement.

This is confirmed by the chromatograms of FIG. 9, comparing the detector response under the some conditions respectively without sensitivity enhancement ($CO_2$ jets in position A and B not operative) and with sensitivity enhancement ($CO_2$ jet in positron A not operative and $CO_2$ jet in position B operative). A series of low concentration impurities in a main component are shown in the chromatograms of FIG. 9, wherein the upper chromatogram shows the main peak together with a series of low concentration impurities in the conventional way, where the lower chromatogram shows how these impurities are collected by means by the single liquid $CO_2$ jet in position B (at the time of valve on) and released as a series of sharp peaks (at the time of valve off) at increased peak intensities.

What is claimed is:

1. A modulator for use in gas chromatographic analysis, adapted for alternatively trapping and releasing fractions of solutes in a length of a capillary column within a chromatographic oven, said modulator comprising at least one nozzle placed to spray at least one jet in at least one corresponding place along said capillary column length, wherein each said nozzle is connected to a source of liquid $CO_2$ via a related valve, and means for alternatively opening said related valve for a predetermined time, to cause a jet of liquid $CO_2$ to impinge for said predetermined time on said column place and to leave the oven atmosphere to heat said column place after said predetermined time.

2. A modulator according to claim 1, each said related valve is alternatively opened for a predetermined time within a given cycle time and wherein said column place is heated by the oven atmosphere during the remaining cycle time.

3. A modulator according to claim 2, for trapping and releasing in sequence fractions of solutes, wherein said modulator comprises at least two nozzles placed to spray liquid $CO_2$ jets in at least two corresponding separated places along said capillary column length, and means for alternatively opening each of said valves associated with said nozzles for a predetermined time in sequence within a given cycle time, to cause each jet of liquid $CO_2$ to impinge for said predetermined time on the corresponding column place and to leave the oven atmosphere to heat said column place during the remaining cycle time.

4. A modulator according to claim 3, wherein said predetermined time is the same for all valves.

5. A modulator according to claim 3, wherein said predetermined time is different for at least two of said valves.

6. A modulator according to claim 4, wherein said predetermined time ranges from about 0.1 seconds to about 30 seconds.

7. A modulator according to claim 4 wherein said cycle time is the sum of the predetermined times of all valves.

8. A modulator according to claim 2, wherein said cycle time ranges from about 0.1 seconds to about 30 seconds.

9. A modulator according to claim 1, wherein each said nozzle has an opening in the form of a slit parallel to said capillary length.

10. A modulator according to claim 9, wherein said slit is about 0.04 mm wide and about 3 mm long.

11. A modulator according to claim 1, wherein each said nozzle is formed by a set of capillaries aligned in parallel to said capillary column length.

12. A modulator according to claim 11, wherein an upstream end of said capillaries open in a common $CO_2$ feeding duct, to which the capillaries are glued or soldered.

13. A modulator according to claim 12, wherein said capillaries each have an inner diameter of the order of 0.11 mm and each set forms a curtain having a length of about 3 mm.

14. A modulator according to claim 1, wherein each said nozzle is inserted in a metal socket.

15. A modulator according to claim 14, wherein said socket is in the form of a brass tube.

16. A modulator according to claim 1, wherein said column length is mounted in stretched conditions.

17. A gas chromatographic analysis method for a comprehensive two dimensional gas chromatographic system having first and second chromatographic columns, said method comprising the steps of:
   (a) providing a modulator having at least one nozzle placed to spray at least one jet in at least one corresponding place along a capillary column length of said first chromatographic column, wherein each said nozzle is connected to a source of liquid $CO_2$ via a related valve, and means for alternatively opening said related valve for a predetermined time, to cause a jet of liquid $CO_2$ to impinge for said predetermined time on said column place and to leave the oven atmosphere to heat said column place after said predetermined time; and
   (b) operating the modulator to modulate solute fractions issued by said first chromatographic column to be fed to said second chromatographic column in a said comprehensive two dimensional gas chromatographic system.

18. A gas chromatographic analysis method for a gas chromatographic system having a chromatographic column and an injector for injecting gas into the chromatographic column, said method comprising the steps of:
   (a) providing a modulator having at least one nozzle placed to spray at least one jet in at least one corresponding place along a capillary column length of said chromatographic column, wherein each said nozzle is connected to a source of liquid $CO_2$ via a related valve, and means for alternatively opening said related valve for a predetermined time, to cause a jet of liquid $CO_2$ to impinge for said predetermined time on said column place and to leave the oven atmosphere to heat said column place after said predetermined time; and
   (b) operating the modulator to modulate injected fractions immediately downstream the injector in a said gas chromatographic system.

19. A gas chromatographic analysis method for a gas chromatographic system having a chromatographic column and a detector for detecting eluting fractions from the chromatographic column, said method comprising the steps of:
   (a) providing a modulator having at least one nozzle placed to spray at least one jet in at least one corresponding place along a capillary column length of said chromatographic column, wherein each said nozzle is connected to a source of liquid $CO_2$ via a related valve, and means for alternatively opening said related valve for a predetermined time, to cause a jet of liquid $C_2$ to impinge for said predetermined time on said column place and to leave the oven atmosphere to heat said column place after said predetermined time; and
   (b) operating the modulator to modulate eluting fractions from a gas chromatographic column immediately upstream of the detector of a said gas chromatographic system.

20. A comprehensive two dimensional gas chromatographic system comprising:
   first and second chromatographic columns operatively connected so that said second chromatographic column receives solute fractions issued by said first chromatographic column; and
   a modulator having at least one nozzle placed to spray at least one jet in at least one corresponding place along a capillary column length of said first chromatographic column, wherein each said nozzle is connected to a source of liquid $CO_2$ via a related valve, and means for alternatively opening said related valve for a predetermined time, to cause a jet of liquid $CO_2$ to impinge for said predetermined time on said column place and to leave the oven atmosphere to heat said column place after said predetermined time, wherein said modulator is operatively positioned with respect to said first and second chromatographic columns so as to modulate the solute fractions issued by said first chromatographic column to be fed to said second chromatographic column.

21. A gas chromatographic system comprising:

a chromatographic column having a capillary column length and an injector for injecting gas into the chromatographic column; and a modulator having at least one nozzle placed to spray at least one jet in at least one corresponding place along a capillary column length of said chromatographic column, wherein each said nozzle is connected to a source of liquid $CO_2$ via a related valve, and means for alternatively opening said related valve for a predetermined time, to cause a jet of liquid $CO_2$ to impinge for said predetermined time on said column place and to leave the oven atmosphere to heat said column place after said predetermined time, wherein said modulator is operatively positioned with respect to said chromatographic column so as to modulate injected fractions immediately downstream of the injector.

22. A gas chromatographic system comprising:

a chromatographic column having a capillary column length and a detector for detecting eluting fractions from the chromatographic column; and a modulator having at least one nozzle placed to spray at least one jet in at least one corresponding place along a capillary column length of said chromatographic column, wherein each said nozzle is connected to a source of liquid $CO_2$ via a related valve, and means for alternatively opening said related valve for a predetermined time, to cause a jet of liquid $CO_2$ to impinge for said predetermined time on said column place and to leave the oven atmosphere to heat said column place after said predetermined time, wherein said modulator is operatively positioned with respect to said chromatographic column so as to modulate the eluting fractions from the gas chromatographic column immediately upstream of the detector.

23. A gas chromatographic system which comprises a chromatographic oven having a capillary column therewithin, and at least one modulator adapted for alternatively trapping and releasing fractions of solutes in a length of the capillary column within the chromatographic oven, said modulator comprising at least one nozzle placed to spray at least one jet in at least one corresponding place along said capillary column length, wherein each said nozzle is connected to a source of liquid $CO_2$ via a related valve, and means for alternatively opening said related valve for a predetermined time, to cause a jet of liquid $CO_2$ to impinge for said predetermined time on said column place and to leave the oven atmosphere to heat said column place after said predetermined time.

* * * * *